United States Patent [19]
Lawin et al.

[11] Patent Number: 5,451,406
[45] Date of Patent: Sep. 19, 1995

[54] TISSUE INJECTABLE COMPOSITION AND METHOD OF USE

[75] Inventors: Timothy P. Lawin, Vadnais Heights; Jeffrey M. Williams, Moundsview, both of Minn.

[73] Assignee: Advanced UroScience, Inc., St. Paul, Minn.

[21] Appl. No.: 274,777

[22] Filed: Jul. 14, 1994

[51] Int. Cl.$^6$ ............................................. A61F 2/02
[52] U.S. Cl. .................................... 424/423; 424/400; 424/484; 514/492; 514/495; 600/30; 604/274
[58] Field of Search ................. 424/423, 400, 484; 514/492, 495; 600/30; 604/274

[56] References Cited

U.S. PATENT DOCUMENTS

| | | | |
|---|---|---|---|
| 3,783,868 | 1/1974 | Bokros | 128/260 |
| 3,977,896 | 8/1976 | Bokros et al. | 427/213 |
| 4,773,393 | 9/1988 | Haber | 600/30 |
| 4,803,075 | 2/1989 | Wallace et al. | 424/423 |
| 5,007,940 | 4/1991 | Berg | 623/66 |
| 5,116,387 | 5/1992 | Berg | 623/66 |
| 5,158,573 | 10/1992 | Berg | 424/423 |
| 5,204,382 | 4/1993 | Wallace et al. | 523/115 |
| 5,258,028 | 11/1993 | Ersek et al. | 623/11 |

OTHER PUBLICATIONS

Walker et al, "InjectableBioglass as a Potential Substitute for Injectable Polytetrafluoroethylene," J. Urol., vol. 148, 645–647, (Aug. 1992).

Kawanabe et al, "Effects of Injecting Massive Amounts of Bioactive Ceramics in Mice," J. of Biomedical Materials Research, vol. 25, 117–128 (1991).

H. S. Borovetz et al, "Protein Adsorption in Vitro Onto Biomaterial Surfaces Covered with Ulti Carbon," Biomaterials, Med. Dev., 10(3), pp. 187–203 (1982).

Al Beavan, "Material Properties and Applications of Pyrolite Carbon," Materials Engineering, (Feb. 1990).

*Primary Examiner*—Gollamudi S. Kishore
*Assistant Examiner*—Pamela S. Webber
*Attorney, Agent, or Firm*—Moore & Hansen

[57] ABSTRACT

An improved biocompatible composition consisting of physiologically stable microparticles carried in a lubricative suspension, solution, other fluid or gel is presented. The composition is intended to be delivered into the body through a small-bore needle, cannula, or catheter and to a tissue site for the purpose of augmenting the tissue site and surrounding area, thereby correcting a defect, filling a void, or strengthening the support structures of the tissue. The particles are a hard, metallic substance and are carbon-coated.

23 Claims, No Drawings

TISSUE INJECTABLE COMPOSITION AND METHOD OF USE

BACKGROUND OF THE INVENTION

This invention relates to an injectable composition of physiologically compatible and appropriately sized particles carried in a lubricative, biologically compatible fluid or gel. The composition is formulated to be delivered into the body to a tissue site through a small-bore instrument to strengthen, bulk-up and otherwise augment the tissue site and surrounding area.

The percutaneous injection of substances into tissues to augment, support, or reconfigure anatomic structure has been the subject of significant research and product development and is well known in the art. See, for example, U.S. Pat. Nos. 4,803,075 and 5,204,382 to Wallace et al and U.S. Pat. No. 5,258,028 to Ersek et al. Procedures have been described in the medical literature for correction of dermatological, otolaryngological problems and for treatment of ufological disorders, e.g., Walker et al., "Injectable Bioglass as a Potential Substitute for Injectable Polytetrafluoroethylene," J. Urol., 148:645–7, 1992 and the references cited therein.

Urinary incontinence and vesicourethral reflux are urological disorders that have responded to treatments with augumentive materials. U.S. Pat. Nos. 5,007,940; 5,158,573; and 5,116,387 to Berg disclose biocompatible compositions comprising discrete, polymeric and silicone rubber bodies injectable into urethral tissue for the purpose of treatment of urinary incontinence by tissue bulking. The most serious adverse effect that may occur from therapies of this type relates to the migration of the solid materials from the original site of placement and into repository sites in various body organs. An important factor in assuring nonmigration is the administration of properly sized particles. If the particle is too small, it is likely to enter the microvasculature system and travel until it reaches a site of greater constriction. Target organs for reposition include the lungs, liver, spleen, brain, kidney, and lymph nodes.

The primary focus of this invention has been directed toward the development of biocompatible, nonmigratory particles that are effectively delivered to the desired tissue site in a lubricative, biocompatible fluid or gel carrier. The preferred carrier shall not cause any deleterious effects at or near the site of particle delivery and will be removed from the site by normal biological or biochemical processes such as excretion or metabolic breakdown.

BRIEF SUMMARY OF THE INVENTION

In accordance with the present invention there is provided an injectable, biocompatible composition comprised of a plurality of discrete, physiologically compatible, carbon-coated particles of a predetermined size range and a lubricative fluid or gel in which the particles are carried. The carrier is preferably a biologically compatible solution or suspension. The particles range in size from 100 microns to 1,000 microns in transverse, cross-sectional dimension.

The composition is designed to be delivered into the body through a small-bore needle, cannula, or catheter and to a tissue site for the purpose of augmenting the tissue site and surrounding area, thereby correcting a defect, filling a void or strengthening the support structures of the tissue.

The invention is comprised of two components.

The first is a plurality of carbon-coated particles ranging in size as microbeads or microparticles from a minimum of 100 microns to a maximum of 1,000 microns. The particles are subjected to a coating process in which carbon is deposited as a thin coating or film on an appropriate, particulate substrate, thereby creating a particle that has a highly biocompatible surface. A hard, metallic substance capable of withstanding the high temperature conditions of the coating process for low temperature isotropic (LTI), pyrolyric carbon is the preferred particulate material. Zirconium oxide has been found to be especially suitable as such a substrate. However, other metallic substrates, including but not limited to medical grade (504) stainless steel, titanium and titanium alloys are also quite acceptable as the substrate material. Gold and silver, which have lower melting temperatures, may be utilized as the particulate substrate in the vacuum vapor deposition process for ultra low temperature isotropic carbon.

The second component acts as the lubricative carrier for the carbon-coated particles and in the preferred embodiment is comprised of a suspension, solution, or other biologically compatible fluid or a gel. Examples of biologically compatible carriers include but are not limited to beta-glucan, hyaluronic acid and derivatives thereof, polyvinyl pyrrolidone or a hydrogel derivative thereof, dextrans or a hydrogel derivative thereof, glycerol, polyethylene glycol, succinaylated collagen, liquid collagen, and other polysaccharides or biocompatible polymers either singly or in combinations with one or more of the above-referenced solutions. The preferred carrier must be capable of being formulated into a viscous fluid or into a self-supporting gel. For purposes of this invention, the carrier shall be of sufficient viscosity to suspend the particles.

DESCRIPTION OF THE PREFERRED EMBODIMENT

The invention consists of an injectable composition that is a combination of a plurality of small, smooth-surfaced particles that are carried in a lubricative fluid or gel that is preferably comprised of a biologically compatible, lubricous solution, suspension, other fluid or gel.

The particles comprise microbeads or microparticles of a hard, material serving as a substrate and having a thin coating or film of biocompatible, isotropic carbon deposited on their surfaces. The substrate material is preferably radiopaque. Different types of carbon coating processes may be utilized, with the particulate substrate being a metallic substance selected for compatibility with the coating process.

Low temperature isotropic (LTI) pyrolyric carbon is a preferred carbon coating. Pyrolytic derives from the term pyrolysis, which is a thermal decomposition of hydrocarbons to produce a carbon material. Pyrolyric carbon is produced in a process in which hydrocarbons and alloying gases are decomposed in a fluidized or floating bed. Inert gas flow is used to float the bed and the substrate particles. The hydrocarbon pyrolysis results in high carbon, low hydrogen content spheres, which deposit as solids upon the substrate in the fluidized bed. As they deposit at temperatures of 1200°–1500° C., the spheres may coalesce, deform, or grow due to atom movement, resulting in a high density coating. A hard, metallic substance capable of withstanding the high temperature conditions of the coating process is the preferred particulate material. Zirconium oxide has been found to be especially suitable as such a substrate. However, other metallic substrates, including but not limited to medical grade stainless steel, titanium and titanium alloys and all oxide derivatives of each, are also quite acceptable as the substrate material.

Ultra-low-temperature isotropic carbon may be applied as a coating in vacuum vapor deposition processes. Carbon can be deposited effectively utilizing ion beams generated from the disassociation of $CO_2$, reactive disassociation in vacuum of a hydrocarbon as a result of a glow discharge, sublimation of a solid graphite source or cathode sputtering of a graphite source, as examples of such processes. Gold has been found to be suitable as a substrate material ideal for vacuum vapor deposited carbon, however, other substrates, including but not limited to nickel, silver, stainless steel, or titanium are also quite acceptable as the substrate material.

Vitreous or glass carbons may also serve as the coating material. These are also isotropic, monolithic carbons, which are formed by pyrolysis of carbonaceous preforms, during which gaseous pyrolysis products diffuse through the shape and are liberated.

The atomic structure of either pyrolitic LTI carbon or vitreous carbon is similar to graphite, the common form of carbon, but the alignment between hexagonal planes of atoms is not as well ordered. Pyrolitic carbon is characterized by a more chaotic atomic structure with warped hexagonal planes, missing atoms and generally a more turbostatic appearance. This results in better bonding between layer planes.

The coating process is applied to small substrate particles to produce final, rounded particles that have a smooth carbon-coated surface in the form of a thin, black film. The resulting smooth surface on the particles enhances their passage through an injection needle, cannula or catheter and into body tissue. The high strength, resistance to breakdown or corrosion, and durability of the carbon coating insures the effective, long term functioning of the particles in tissue augmentation at the injection site. The established biocompatibility of pyrolytic carbon renders it particularly suitable for the anticipated body tissue applications.

After the carbon coating has been applied, the particles are subjected to a cleaning and sieving process to remove contaminants and to separate out particles of a size less than or greater than the desired size range. The particles may range in size from 100 microns to 1,000 microns in average, transverse cross-sectional dimension, and a preferred size range is between 200 and 500 microns. That size avoids particle migration from the injection site and facilitates injection through a small bore instrument. The substrate particles are initially milled, extruded or otherwise formed to the desired particle size, in a substantially rounded shape prior to being subjected to the coating process. The particles are randomly shaped and rounded, ranging from oblong to generally spherical. The sieving process is such that the minimum particle dimension will pass through a U.S. No. 18 Screen Mesh (1000 micron grid size opening) but will not pass through a U.S. No. 140 Screen Mesh (106 micron grid size). That minimum dimension will be the transverse, cross-sectional dimension on oblong or elongated particles, with that dimension coinciding with the particle diameter on generally spherical particles.

The carrier is preferably an aqueous suspension or solution, other fluid or gel of polymeric chains of B-D-glucose, commonly referred to as B-glucan. The glucose units are linked to each other at the 1-3, 1-4, or 1-6 positions and form polymeric chains ranging to several thousand daltons in weight.

B-glucan is a naturally occurring constituent of cell walls in essentially all living systems including plants, yeast, bacteria, and mammalian systems. Its effects and modulating actions on living systems have been studied extensively (see Abel, G., and Czop, J. K., "Stimulation of Human Monocyte B-Glucan Receptors by Glucan Particles Induces Production of TNF-∂ and 1L-B" *Int. J. Immunopharmacol.,* 14(8):1363-1373, 1992 and references included therein). B-glucan, when administered in experimental studies, elicits and augments host defense mechanisms including the steps required to promote healing by first intent, thereby stimulating the reparative processes in the host system. B-glucan is rapidly removed from tissue sites through macrophagic phagocytosis or by enzymatic destruction by serous enzymes. The rapid destruction or removal of B-glucan, as well as its available viscosity and lubricous nature, makes it an optimum carrier for the particles.

Aqueous solutions, suspensions, fluids, or gels of B-glucan can be produced that have favorable physical characteristics as a carrier for carbon-coated particles. The viscosity can vary from a thin liquid to a firm, self-supporting gel. Irrespective of viscosity, the B-glucan has excellent lubricity, thereby creating a particle-carrier composition which is easily administered by delivery to a predetermined body site through a small bore needle, cannula, or catheter. The carrier will be of sufficient viscosity to assure that the carbon-coated particles remain suspended therein. Other examples of appropriate carriers include hyaluronic acid, polyvinyl pyrrolidone or a hydrogel derivative thereof, dextran or a hydrogel derivative thereof, glycerol, polyethylene glycol, succinylated collagen, liquid collagen, oil based emulsions such as corn oil or safflower, or other polysaccharides or biocompatible organic polymers either singly or in combination with one or more of the above-referenced solutions.

In use, the above-described composition will be injected in a fluid state, e.g., as a slurry, fluid suspension or emulsion, or as a gel through a syringe needle or cannula into a body tissue site. When deposited into a soft tissue site, the preferred B-glucan carrier will disperse or be destroyed as set forth above. The particles are of an optimum size which will prevent their being carried away by capillary blood flow. They will thus remain at the site and will serve to fill voids, provide additional support, or correct other soft-tissue defects. For urological applications, the composition may be injected into the tissue of the urinary tract, wherein the selected site may be, for example, the bladder neck, the urethra or urethral sphincter. The resulting bulking or augmentation of the urethral tissue will restrict the size of the urethra or urinary passage and thus assist in overcoming incontinence.

In an experimental study, a syringe was utilized to contain and inject a fluid composition comprised of:
  pyrolyric isotropic LTI carbon-coated zirconium oxide particles in a size range from 200 to 500 microns of a total mass of 400 mg suspended in;
  B-glucan formulated as a 1% weight by weight aqueous suspension, as the carrier.

The test composition was administered by periurethral injection into dogs. Injections were performed such that the bulk of the bladder neck/periurethral tissue was increased but such that the urethral lumen diameter was not compromised. One or more injections of the test material were administered in total volumes ranging from 1.9 to 2.5 milliliters.

The study was conducted in accordance with good laboratory practices and confirmed that the handling characteristics of the test material were favorable, as the material was easily injected with minimal to moderate resistance. No evidence of migration of the implant material was noted.

What is claimed is:

1. An injectable, biocompatible composition for tissue augmentation comprising:
    a plurality of discrete particles in a carrier, wherein the particles are substrate particles with a carbon coating and have an average, transverse cross-sectional dimension of between 100 and 1,000 microns and the carrier is a biocompatible medium having sufficient fluidity to carry and deliver the particles, and has lubricative qualities.
2. The composition of claim 1 wherein:
   said substrate particles are a metallic substance.
3. The composition of claim 1 wherein:
   the substrate particles are selected from the group comprising stainless steel, titanium and titanium alloys, and their oxides.
4. The composition of claim 1 wherein:
   said carbon coating is isotropic carbon.
5. The composition of claim 1 wherein:
   said substrate particles are zirconium oxide.
6. The composition of claim 4 wherein:
   said isotropic carbon coating is low temperature isotropic (LTI), pyrolyric carbon.
7. The composition of claim 6 wherein:
   said substrate particles are zirconium oxide.
8. The composition of claim 4 wherein:
   said isotropic carbon coating is ultra low temperature isotropic carbon which is vapor deposited.
9. The composition of claim 1 wherein:
   said carbon coating is pyrolyric, isotropic carbon.
10. The composition of claim 8 wherein:
    said substrate particles are gold or silver.
11. The composition of claim 1 wherein:
    said carbon coating is a smooth, surface film.
12. The composition of claim 4 wherein:
    said coating is a smooth, surface film.
13. The composition of claim 4 wherein:
    said carbon coating is vitreous carbon.
14. The composition of claim 11 wherein:
    said substrate particles are zirconium oxide.
15. The composition of claim 4 wherein:
    said substrate particles are of rounded shape and said dimension is between 200 microns and 500 microns.
16. The composition of claim 1 wherein:
    the substrate particles are radiopaque.
17. The composition of claim 1 wherein:
    the carrier is a solution, suspension or gel of polysaccharides.
18. The composition of claim 17 wherein:
    the polysaccharide is beta-glucan.
19. The composition of claim 1 wherein:
    the carrier is a solution or suspension selected from the group comprised of hyaluronic acid, polyvinyl pyrrolidone or a hydrogel derivative thereof, dextran or a hydrogel derivative thereof, glycerol, polyethylene glycol, succinylated collagen, liquid collagen, or other polysaccharides or biocompatible organic polymers, either singly or in combination.
20. A method for augmenting tissue in a human patient comprising injecting into a tissue site in the patient a composition comprising a plurality of discrete, carbon coated substrate particles having an average, transverse, cross-sectional dimension of between 100 and 1,000 microns in a biocompatible carrier having sufficient fluidity to carry and deliver the particles and lubricative qualities.
21. The method of claim 20 wherein the tissue site is in the urinary tract.
22. The method of claim 21 wherein the tissue site is the urinary sphincter muscle.
23. The method of claim 21 wherein the tissue site is the urethra.

* * * * *

UNITED STATES PATENT AND TRADEMARK OFFICE
CERTIFICATE OF CORRECTION

PATENT NO. : 5,451,406
DATED : Sep. 19, 1995
INVENTOR(S) : Lawin et al.

Page 1 of 2

It is certified that error appears in the above-indentified patent and that said Letters Patent is hereby corrected as shown below:

col. 1, line 22, after the words, "treatment of," delete "ufological" and substitute --urological-- therefor.

col. 2, line 11, after the words, "isotropic (LTI)," delete "pyrolyric" and substitute --pyrolytic-- therefor.

col. 2, line 54, after the words, "isotropic (LTI)," delete "pyrolyric" and substitute --pyrolytic-- therefor.

col. 2, line 57, after the words, "carbon material." delete "Pyrolyric" and substitute --Pyrolytic-- therefor.

UNITED STATES PATENT AND TRADEMARK OFFICE
CERTIFICATE OF CORRECTION

PATENT NO. : 5,451,406
DATED : Sep. 19, 1995
INVENTOR(S) : Lawin et al.

It is certified that error appears in the above-indentified patent and that said Letters Patent is hereby corrected as shown below:

col. 4, line 60, after the words, "comprised of:" delete "pyrolyric" and substitute --pyrolytic-- therefor.

col. 5, line 40, after the words, "coating is," delete "pyrolyric" and substitute --pyrolytic-- therefor.

Signed and Sealed this

Twenty-third Day of April, 1996

Attest:

BRUCE LEHMAN

*Attesting Officer*  *Commissioner of Patents and Trademarks*